(12) United States Patent
Bond

(10) Patent No.: US 8,529,982 B2
(45) Date of Patent: Sep. 10, 2013

(54) FINGERPRINT DETECTION

(75) Inventor: John Bond, Northhamtpon (GB)

(73) Assignee: Northamptonshire Police Authority, Northamptonshire (GB)

( * ) Notice: Subject to any disclaimer, the term of this patent is extended or adjusted under 35 U.S.C. 154(b) by 63 days.

(21) Appl. No.: 13/125,460

(22) PCT Filed: Oct. 23, 2009

(86) PCT No.: PCT/GB2009/002540
§ 371 (c)(1),
(2), (4) Date: Aug. 8, 2011

(87) PCT Pub. No.: WO2010/046665
PCT Pub. Date: Apr. 29, 2010

(65) Prior Publication Data
US 2012/0036946 A1  Feb. 16, 2012

(30) Foreign Application Priority Data
Oct. 23, 2008  (GB) .................................. 0819445.8

(51) Int. Cl.
*A61B 5/103*  (2006.01)
(52) U.S. Cl.
USPC ............................................................. 427/1
(58) Field of Classification Search
None
See application file for complete search history.

(56) References Cited

U.S. PATENT DOCUMENTS

| 4,258,073 A | 3/1981 | Payne |
| 5,079,029 A | 1/1992 | Saunders |
| 5,543,334 A * | 8/1996 | Yoshii et al. ..................... 438/17 |
| 5,959,461 A * | 9/1999 | Brown et al. ............... 324/750.2 |
| 6,592,929 B1 | 7/2003 | Berka et al. |
| 2009/0185725 A1 | 7/2009 | Bond |

FOREIGN PATENT DOCUMENTS

| GB | 1500592 | 2/1978 |
| GB | 2015430 A | 9/1979 |

OTHER PUBLICATIONS

Thomas, The physics of fingerprints and their detection, J.Phys.E: Sci, Instrum., vol. 11 (1978).
International Search Report, PCT/GB2009/002540 (Jan. 21, 2010).

* cited by examiner

*Primary Examiner* — Robert R Raevis
(74) *Attorney, Agent, or Firm* — Caesar, Rivise, Bernstein, Cohen & Pokotilow, Ltd.

(57) ABSTRACT

The invention relates to an apparatus for and a method of detecting latent fingerprints on a previously heated substrate, such as a bullet casing following discharge of a bullet. By applying a potential difference across the substrate, and contacting the substrate with detection means, such as graphite coated beads, arranged to selectively attract to or repel from the area of a latent fingerprint on the surface, a latent fingerprint may be recovered.

15 Claims, 6 Drawing Sheets

FINGERPRINT DETECTION

CROSS-REFERENCE TO RELATED APPLICATIONS

This application is a national stage application that claims the benefit under 35 U.S.C. §371 of International Application No. PCT/GB2009/002540 filed on Oct. 23, 2009, which in turn claims priority to British Application No. 0819445.8 filed on Oct. 23, 2008.

This invention relates generally to apparatus for and methods of detecting fingerprints. More specifically, but not exclusively, the invention relates to an apparatus for and a method of detecting latent fingerprints.

BACKGROUND OF THE INVENTION

It is widely known to locate and detect fingerprints deposited on metal or other surfaces using chemical reactions with either the eccrine (amino acid) and/or sebaceous (fatty acid) content of a fingerprint residue. Other methods of detecting fingerprints involve solvent techniques, e.g. cyanoacrylate fuming, or using the fingerprint residue as an insulator against electrochemical or reduction/oxidation (redox) reactions.

Such methods require the continued presence of the fingerprint residue and are not suitable for the visualisation of latent fingerprints.

Another known technique for detecting residual fingerprints measures the difference in electrical potential between a metal substrate on which a fingerprint has been deposited and a metal probe not in contact with the surface. The technique exploits a discovery made by Lord Kelvin in the nineteenth century, which is that different metals, connected electrically, have a potential difference between them determined by the work function of the metals. The work function of a particular metal is a measure of the ease with which an electron can leave the surface of the metal. The chemicals found in a fingerprint deposit cause corrosion of a metallic surface. The work function of a metal changes where it has been corroded by a fingerprint. Therefore a work-function based technique relies on measuring the differences in work function across the whole of a surface of a metal where it is suspected a fingerprint has been deposited. Clearly, this can be a time consuming and haphazard process.

The effects of increased temperature on a substrate are known to inhibit subsequent fingerprint detection. This is in part due to the eccrine and sebaceous content of the residue becoming evaporated and/or vapourised at high temperature.

In addition, a surface can become wet, e.g. from lying for sometime on the floor during wet weather, which may result in the residual fingerprint being washed from a substrate. Moreover, the perpetrator of a crime may have gone to his best efforts to disguise his identity by wiping or washing away his fingerprint from the substrate.

One particular problem has been trying to detect and develop fingerprints on small objects with tightly curved surfaces, e.g. brass shell casings. Due to the tight curvature of the surface, even when handled, a whole fingerprint is rarely deposited.

It is desirable to be able to locate and identify whole or partial fingerprints deposited on a wide variety of surfaces even when such surfaces have been exposed to extreme or outdoor conditions or have been cleaned, for example by persons trying to hide their actions.

SUMMARY OF THE INVENTION

The present invention seeks to avoid or mitigate at least one or more of the problems described above by providing an apparatus for and method of detecting latent fingerprints which is suitable for use on metal surfaces, e.g. discharged brass shell casings, Improvised Explosive Devices (IEDs) where the fingerprint residue has been diminished, e.g. by heating, washing or other treatment.

According to one aspect of the invention, there is provided a method of detecting a latent fingerprint on a previously treated substrate, the method comprising applying a potential difference across the substrate and contacting the substrate with detection means arranged to selectively attract to or repel from the area of a latent fingerprint on the surface.

According to another aspect of the invention, there is provided apparatus to detect a latent fingerprint on a substrate, the apparatus comprising delivery means for the delivery of detection means and support means, for supporting a substrate, said delivery means and said support means having an electrical potential applied thereto.

The apparatus preferably comprising means to rotate a substrate.

There may be provided means to retain a substrate within, on or abutting the apparatus.

A resiliently urged contacting means may be provided to contact a substrate.

Said delivery means may be adjustable.

Preferably said delivery means is adjustable to alter the angle between the delivery means and a substrate, e.g. by tilting. Such adjustability may be used to alter the angle and/or speed at which said detection means contacts a substrate.

Said detection means may comprise ceramic beads, e.g. beads coated with a conductive powder.

In one embodiment the apparatus may comprise a pair of adjustable supports arranged to provide a guide for reception of at least part of a substrate.

A further aspect of the invention provides a method of detecting a latent fingerprint or part thereof on a discharged shell casing or part of a discharged explosive device, the method comprising applying a potential difference across the shell casing or part of a discharged explosive device and contacting the surface thereof with detection means arranged to selectively attract to or repel from an area of a latent fingerprint or part thereof on the surface.

Other tightly curved substrates may be detected.

Other substrates which have been in harsh environments to remove or obliterate fingerprint residues, or parts thereof may be detected. Harsh environments include high temperatures, contact with aqueous and/or organic solvents, abrasion (e.g. rubbing) and so on.

The method may comprise heating a substrate prior to applying the potential difference.

The method may comprise washing, and/or cleaning a substrate prior to applying the potential difference.

The term "latent fingerprint" is intended to mean a fingerprint residue that has been removed subsequent to its deposition, e.g. been removed or obliterated, e.g. by harsh environments or a person trying to hide their actions.

BRIEF DESCRIPTION OF SEVERAL VIEWS OF THE DRAWINGS

Exemplary embodiments of the invention will now be described by way of example only and with reference to the accompanying drawings, in which.

DETAILED DESCRIPTION OF PREFERRED EMBODIMENTS

Figure 1:
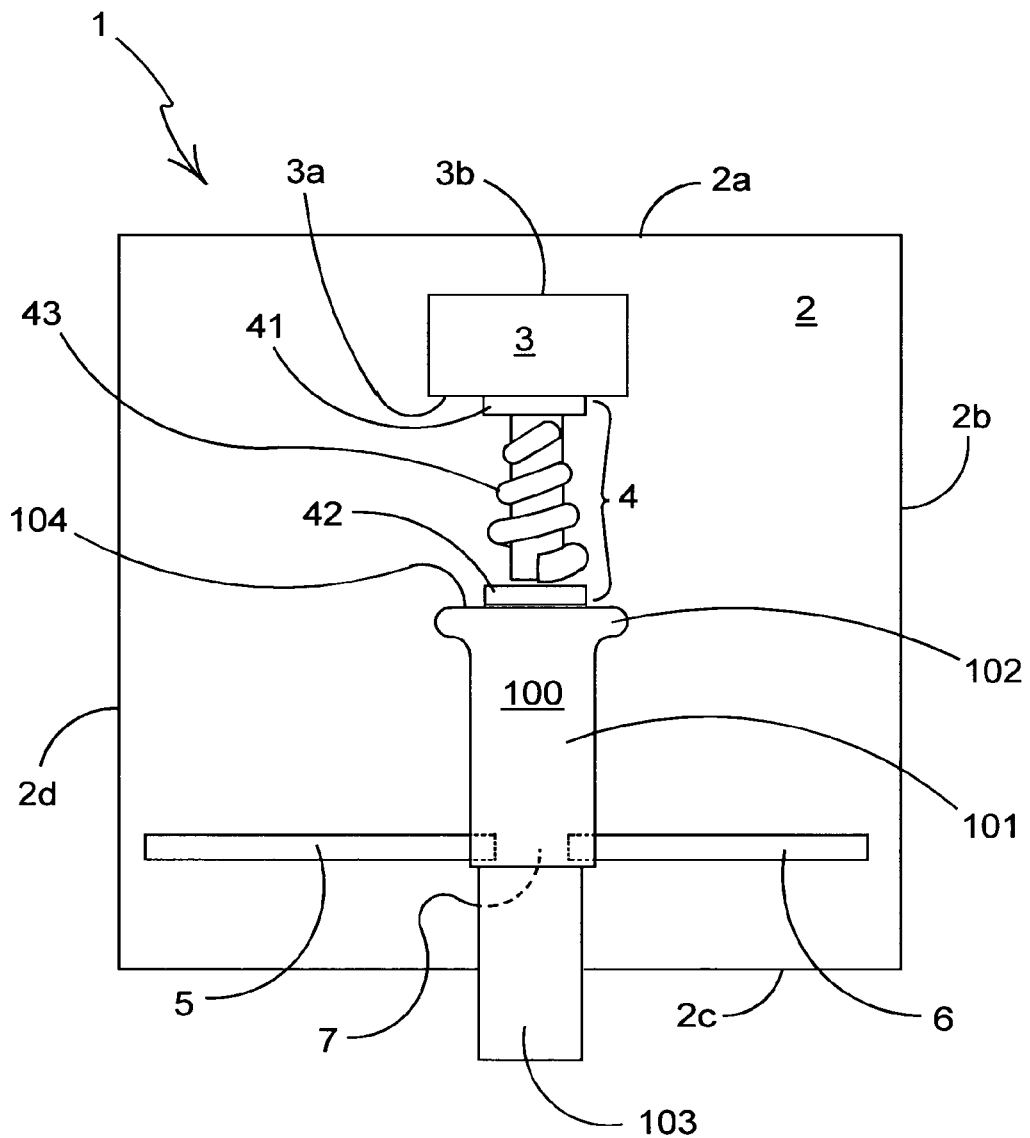
FIG. 1 shows a plan view of apparatus according to the present invention.
Figure 2:
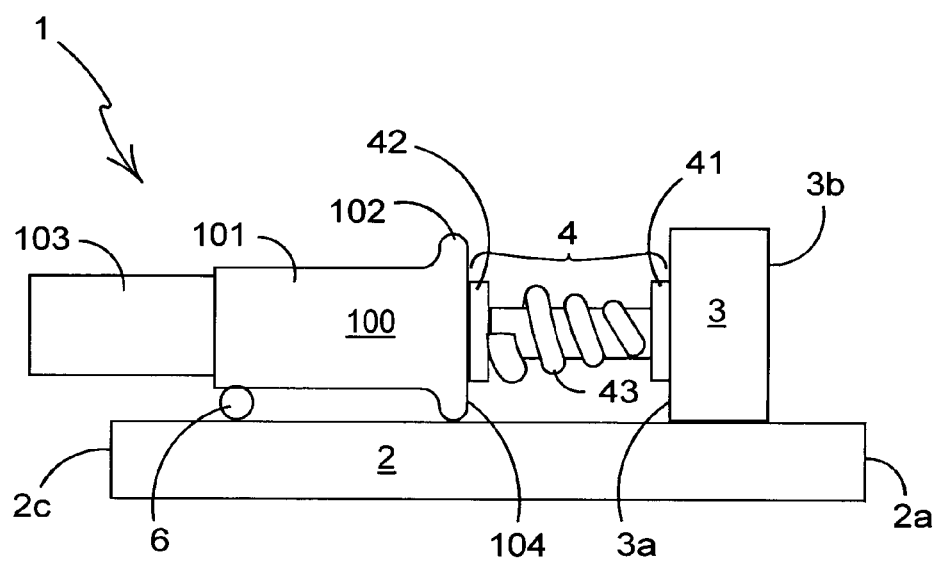
FIG. 2 shows a side elevation of the apparatus of FIG. 1.
Figure 3:
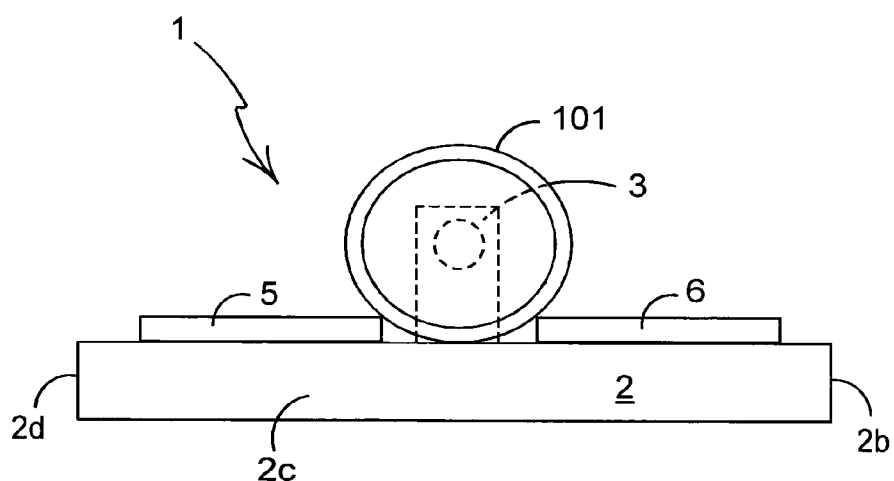
FIG. 3 shows a front elevation of the apparatus of FIG. 1.

Referring first to FIGS. 1, 2 and 3 there is shown apparatus 1 according to the present invention.

The apparatus 1 comprises a base portion 2, which is substantially flat, an upstanding portion 3, a plunger 4 and a pair of spaced longitudinal ribs 5, 6.

The base portion 2 is substantially square and comprises four edges 2a to 2d. The base portion 2 is at least part made from a conductive material, e.g. metal. The remaining part may be made from any other suitable material, e.g. a non-conductive material such as wood.

The upstanding portion 3 upstands from the base portion 2 (as shown in FIG. 2) at a location inboard the peripheral edge 2a of the base portion 2.

The upstanding portion 3 comprises two major faces; a first major face 3a and a second major face 3b. The first and second major faces 3a, 3b are parallel to the parallel edges 2a, 2c of the base portion 2.

Mounted to the first major face 3a of the upstanding portion 3 is a first contact member 41 to which is mounted a first end of a compression spring 43 and to the other end of the compression spring 43 is provided a second contact member 42. Thus the second contact member 42 is resiliently urged away from the first contact member 41.

The longitudinal ribs 5, 6 are aligned parallel to each other along a common principal axis and are located inboard the peripheral edge 2c of the base portion 2. The ribs 5, 6 upstand from the base portion 2 and run parallel to its edges 2a, 2c. The ribs 5, 6 are aligned such that there is a discontinuity 7 present between the adjacent ends of corresponding ribs 5, 6.

In use, a sample material, e.g. a discharged brass shell casing 100, is introduced to the apparatus 1.

The casing 100 comprises a cylindrical body portion 101, a circumferential rib 102 and an opening (not shown). The circumferential rib 102 is located at the closed "strike" end 104 of the casing 100.

A longitudinal member 103, e.g. a wooden rod, machined to provide a to friction fit is located within the cylindrical body portion 101 through, the opening.

The longitudinal member 103 with casing 100 fitted thereon is introduced to the apparatus 1 by bringing the closed end 104 of the casing 100 into contact with the second contact member 42. A portion of the cylindrical body 101 rests within the discontinuity 7. The spacing between the ribs 5, 6 can be adjusted to accommodate larger or smaller samples, e.g. casings 100 of different calibres.

At least a part of the base portion 2, the upstanding portion 3, the plunger 4 and the ribs 5, 6 are all made from a conductive material, e.g. a metal, for example, brass or any other suitable conductive metal.

Figure 4:
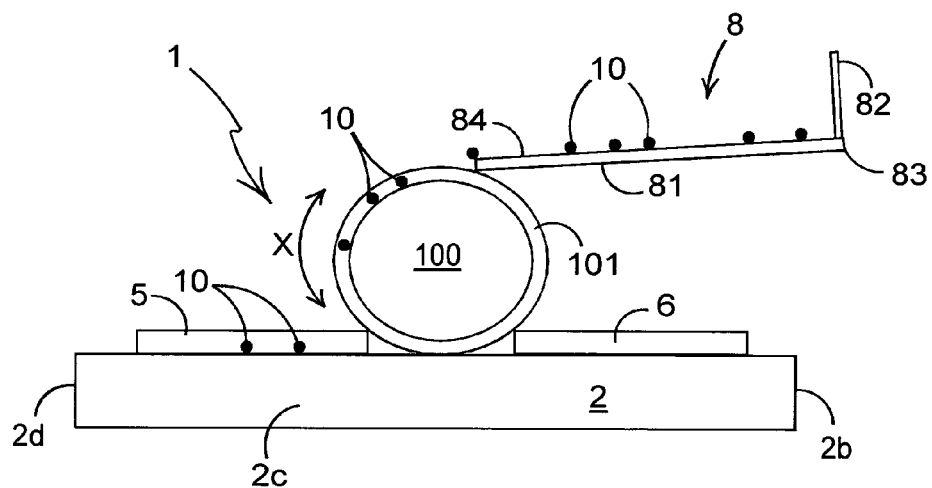
FIG. 4 shows a front elevation of the apparatus of FIG. 1.

Referring to FIG. 4, the apparatus 1 further comprises a receptacle 8. The receptacle 8 comprises a substantially horizontal portion 81 and an upstanding portion 82.

Figure 5:
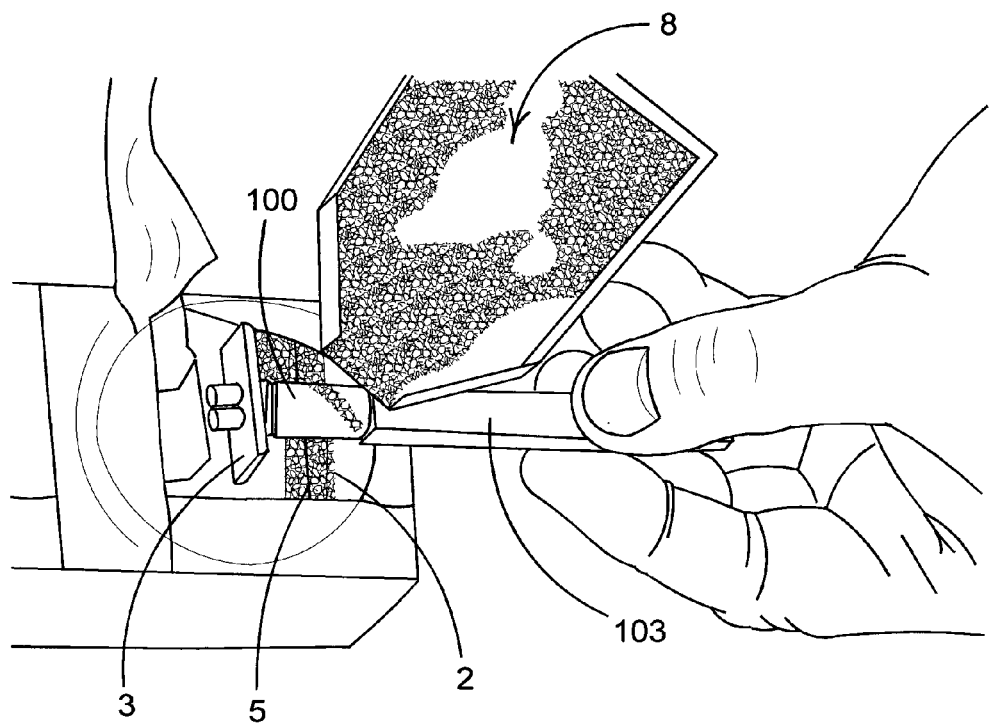
FIG. 5 shows a perspective view of the apparatus according to FIG. 4.

As can be seen from FIG. 5 the upstanding portion 82 extends around most of the periphery of the receptacle 8, but provides an opening 84.

A shown in FIG. 4, the opening is in contact with the body portion 101 of the casing 100.

The receptacle 8 is made of a conductive material e.g. metal, for example, brass or any other suitable conductive metal.

The receptacle 8 is capable of holding ceramic spherical beads 10, for example, beads 10 of approximately 10 microns in diameter, which are coated in a fine granular (~2 micron) black conducting powder, e.g. carbon conducting powder. The coated ceramic spherical beads 10 are known in the art and are commercially available.

In operation a casing 100 which may have a latent fingerprint thereon has a rod 103 fitted therein and is brought into contact with the second contact member 42. An electric potential of 2.5 kV is applied to the base portion 2. As all contacting parts are conductive the apparatus 1, as a whole, has the potential applied thereto.

The exemplary method described and depicted herein involves applying an electrical potential of the order of 2.5 kV, with respect to earth, to a metallic sample, e.g. a brass casing 100, upon which a latent fingerprint, or part thereof, has been deposited.

It has been observed that the higher the voltage the better the observed affect and, therefore, many voltages other than 2.5 kV will create a differential charge density sufficient to enable a latent fingerprint to be detected and identified.

The rod or longitudinal member 103 enables the casing 100 to be revolved (as shown by X in FIG. 4) whilst maintaining an electrical contact with the plunger 4 and the ribs 5, 6.

In operation beads having conducting powder, e.g. a carbon conducting powder, thereon are located in the receptacle 8.

The receptacle 8, shown in FIG. 4 connected to the casing 100, is adjustable, e.g. it can be tilted to encourage the ceramic beads 10 to roll towards the casing 100. The beads 10 are brought into contact with the casing 100. Introducing the beads 10 from an adjustable receptacle 8, rather than directly, overcomes the problem of the beads 10 depositing carbon powder at the point of impact with the casing 100. By turning the longitudinal member 103, the casing 100 can be rotated whilst applying the beads 10 from the receptacle, thereby exposing the entire surface of the casing 100 to the beads 10.

The ceramic spherical beads 10 act as a carrier for the conducting powder onto the casing 100. The ceramic beads 10 are spherical so they can easily move across the surface of the casing 10.

The beads 10 roll across the surface of the casing 10, as they do so the conducting powder is attracted to areas that have different electrical properties to the surrounding area. Therefore, on contact with a latent fingerprint, the lower potential of the area corroded by a fingerprint residue attracts the conducting powder from the beads 10 onto that part of the metal surface.

Figure 6:
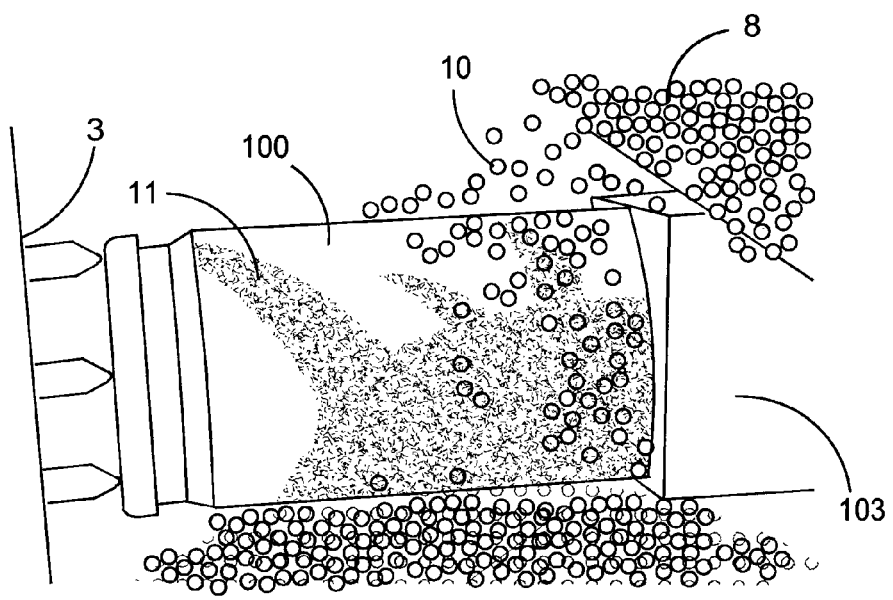
FIG. 6 shows a detailed view of the apparatus according to FIG. 5.

FIGS. 5 and 6 show the method of the present invention being applied to a brass shell casing 100. The longitudinal member 103 is non-conducting, e.g. wood, and is rotated, simultaneously, with the tilting of the receptacle 8 containing the beads 10.

Figure 7:
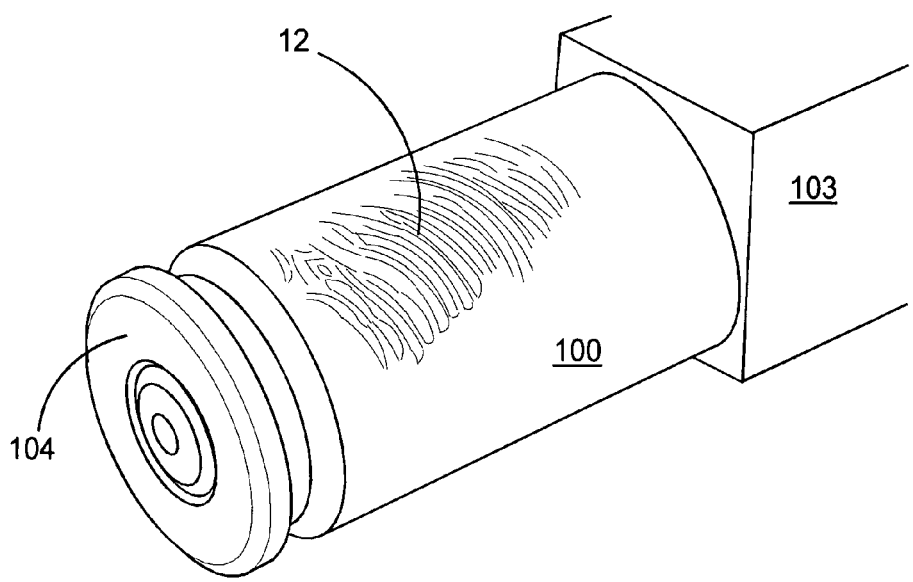
FIG. 7 shows a perspective view of a partial ridge detail development of a latent fingerprint.

In FIG. 7 an otherwise undetectable latent fingerprint 12 is exposed. The black powder can be lifted according to known techniques.

It is shown that after using electrostatic enhancement, the partial fingerprint 12 can be detected and identified, whereas prior to using the method and apparatus 1 the fingerprint 12 could not be seen.

After electrostatic treatment, the conducting powder may be vulnerable to disturbance once the electric potential has been removed. By heating the sample material (the casing 100) after treatment to a temperature of, for example 150° C., the conducting powder will bind to the casing 100, thereby producing a more durable sample.

It is to be appreciated by the skilled addressee that whilst the method using the apparatus 1 of the present invention is carried out manually, it may also be automated, e.g. by using a robot, without departing from the scope of the present invention. It is also to be appreciated that a catch means (not shown) may be provided on or within the apparatus 1 to ensure that the casing 100 and second contact member 42 remain abutting without the need for the operator to be present.

Example 1

Four 9 mm brass shell casings 100 were obtained which were retained as part of an ongoing investigation. These casings 100 were subjected to a visual examination for fingerprints followed by cyanoacrylate fuming. Each casing was then treated with Blitz™ fluorescent powder. No fingerprints were visualised on any of the four casings 100.

Fourteen years after the incident and the original examination of the fingerprints, the four casings 100 were re-examined.

Initially, a visual examination confirmed that no fingerprint ridge detail was apparent on the casings 100. In view of this, each casing was heated (to a temperature of ~700° C.) over an open flame. This was done for two reasons:

(1) To remove any fumed cyanoacrylate deposit that may have been adhering to the surface of the casings 100.

(2) To induce a corrosive reaction between the brass surface of the casing 100 and ionic salts present in any residual fingerprint deposit remaining on the surface of the casing 100.

Each casing 100, in turn, was subjected to the method of the present invention (as described above). The conducting powder was found to adhere to a small area of one casing 100.

Subsequently, the casing 100 was heated to a temperature of 150° C. in order to "bake" the conducting powder onto the surface of the casing 100 and thus provide a more durable image.

Despite both the time elapsed since the incident and the previous cyanoacrylate fuming of the shell casings, fingerprint ridge lines were visualised by means of carrying out a method according to the present invention.

Clearly, the method of the invention is capable of developing fingerprints after a significant period of time.

The method relies on the corrosion of the metallic sample surface subsequent to the deposition of a whole or part of a fingerprint residue, however, the method does not rely on the continued presence of the residue (i.e. the residue, or part thereof, may be removed, e.g. by cleaning, increasing the temperature or by abrasive friction). The applied potential creates a charge density across the surface of the casing 100. At the place where a whole or part of a fingerprint residue had existed prior to its removal (or part removal) the charge density differs from the charge density of the surrounding area. In other words, the sample surface has a memory of the contours of the deposited residue.

The memory is a result of a corrosive reaction occurring between the metal surface of the casing 100 and the residue deposited on the surface, e.g. a redox reaction between ionic salts present in the residue and the metal surface of the casing 100.

Electric potential is provided, in use, by a high voltage unit (not shown), based around a Brandenburg 3590 series high voltage module. The unit enables the generation of a continuously variable potential from 0-2.5 kV.

Other high voltage modules may be used which generate different potentials.

It should be clear to a person skilled in the art that the present invention is not limited solely to the application of a potential voltage of 2.5 kV and that lower or higher potentials may be applied.

Visualisation of latent fingerprints on discharged shell casings 100 can provide good forensic evidence, particularly if the casing 100 is recovered at the scene of a crime where a firearm has been discharged. In these circumstances, a fingerprint 12 can link an individual to the casing 100 before it was loaded into the firearm and hence, potentially, provide a link to the perpetrator of the crime.

Figure 8:
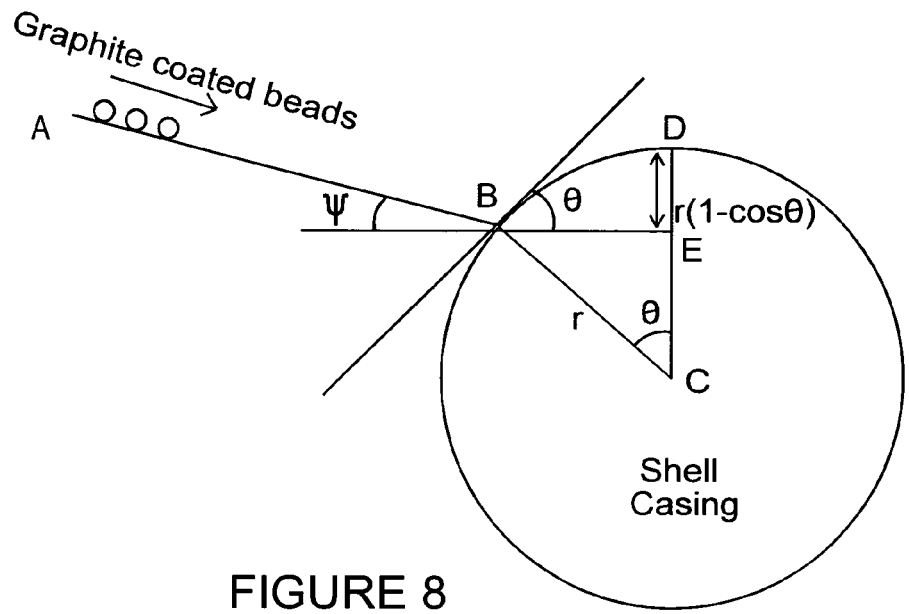
FIG. 8 shows a schematic diagram of a part of a second embodiment of apparatus according to the present invention.
Figure 9:
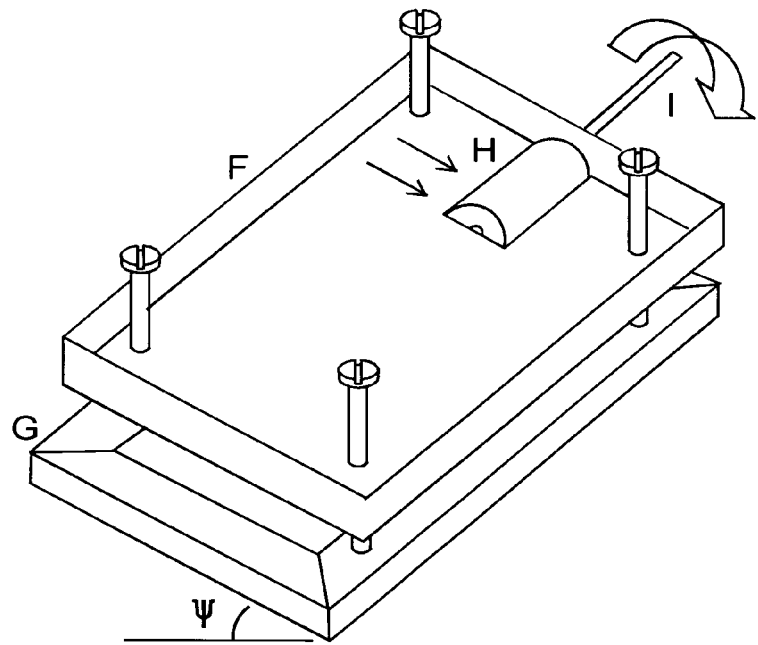
FIG. 9 shows a schematic diagram illustrating more fully the second embodiment of the invention.
Figure 10:
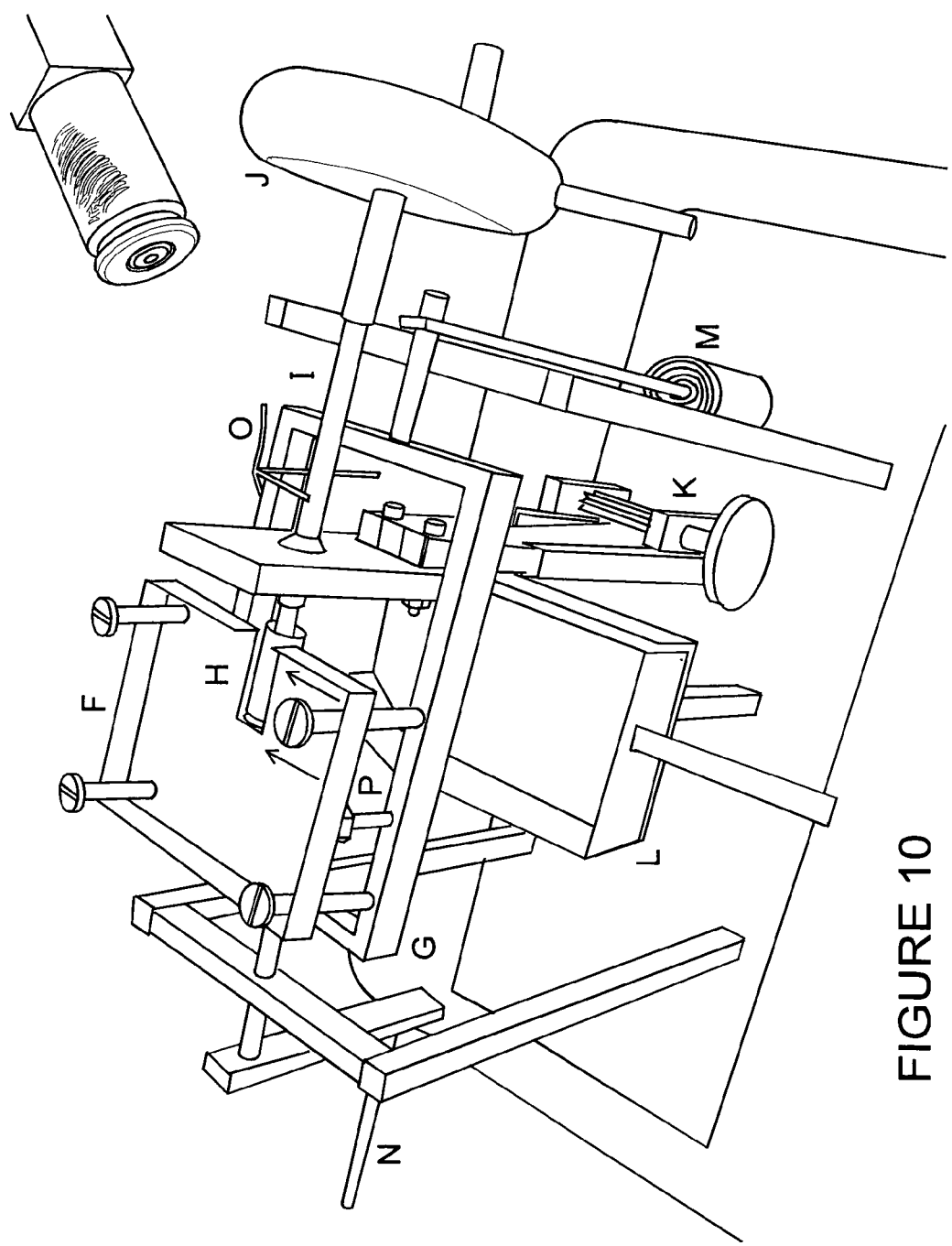
FIG. 10 shows more fully still the second embodiment of FIGS. 8 and 9.

Referring now to FIGS. 8, 9 and 10 a second embodiment of the present invention will be described. While utilizing the same principle as the first embodiment, the second embodiment seeks to reduce unwanted deposition of the coating powder onto the shell casing at the point of contact between the casing and the coating powder. The second embodiment enables the beads of the coating powder to be rolled gently over the surface of the shell casing while the casing is rotated.

The operating principle of the instrument is based on the angle of contact between a planar surface containing coated spherical beads and the shell casing preventing unwanted deposition of graphite onto the casing. Consider the schematic representation of this angle of contact ($\theta$) in FIG. 1, which shows coated beads rolling down an incline AB at an angle $\psi$ to the horizontal. The beads meet the shell casing (radius=r) at a contact angle $\theta$ to the horizontal. The vertical distance from the point at which the beads meet the casing to the top of the casing is given by DE=r (1−cos $\theta$).

For the beads not to deposit the coating on contact with the casing the electrostatic force of attraction between the graphite coating and the bead must be greater than the deceleration force experienced as the beads begin to move along the arc BD. Assuming the charge on the surface of a spherical bead is distributed symmetrically, the electrostatic force of attraction between the graphite (in contact with the bead) and the bead is given by $$F^0 = qq_0/4\pi\epsilon\epsilon_0 r^2,$$

in which q and $q_0$ are the charge on the graphite and bead respectively, $\epsilon$ is the relative permittivity of the bead and $\epsilon 0$ is the relative permittivity of free space. As the graphite is thinly distributed (in the form of beads) over the surface of the bead the above equation, F0 assumes no contribution from the other graphite particles on the bead. The initial deceleration when a bead makes contact with the casing at point B is the sum of forces due to gravitational deceleration and the attraction between the bead and the positively charged brass surface. For an applied potential to the brass of 2.5 kV, the force due to gravitational deceleration is much greater than that due to the attraction between the bead and brass surface. Thus, the force acting on a graphite particle can be approximated to $$F^1 = mg \sin \theta$$

where m is the mass of the graphite particle and g is acceleration due to gravity. To prevent graphite deposition on contact $F^0 > F^1$ and two equations above may be solved to give a maximum value for $\theta$. On the basis that the radius of the spherical bead and graphite particle are 250 and 5 μm respectively ε=3.8 and from reported measurements of q and q0, θ<41°.

In addition from FIG. 8 the angle of inclination (ψ) the planar surface AB determines the velocity at which the bead makes contact with the shell casing. This velocity must be sufficient to enable the bead to traverse the arc BD and reach the top of the casing. Thus, assuming the start velocity of the bead on AB is zero, there is a minimum value for ψ to achieve this. Knowing the distances BD and AB and taking the above assumptions, the equations of motion give a minimum value for ψ.

The validity of these calculations for θ has been confirmed using the apparatus shown in FIGS. 9 and 10. A brass tray F was positioned on a conductive frame, for example of brass, G such that the angle of inclination of the tray can be adjusted by brass shaft I such that the shaft could be rotated about its axis, thereby rotating the shell casing. Final positioning of the shell casing was achieved by means of a micromanipulation stage, consisting of two orthogonally arranged linear bearings, to leave a gap between the shell casing and sides of the aperture of ~0.1 mm. A potential of 2.5 kV was then applied to both the test rig and the shell casing. Graphite coated beads were introduced to the tray 2 cm from the aperture and traveled toward the aperture, as shown by the arrows in FIG. 9. For a given aperture (and θ) the shell casing was rotated 10 revolutions, while beads were fed continuously into the tray. After 10 revolutions, the graphite particles adhering to the shell casing were collected by washing the casing in a known mass of water, which was evaporated prior to weighing. This process was repeated ten times for each aperture and an average mass of graphite particles calculated for each aperture. This process was repeated with five different apertures (33°≦θ≦52°). The result indicate that for θ>~40° (DE>~2 mm), the deposition of graphite particles increases rapidly to a level similar to that of the first embodiment.

With reference to FIG. 10, in normal operation, for a 9 mm shell casing, the brass tray (F) is positioned with ψ≈10° and DE (from FIG. 8) ≈1.5 mm. The shell casing is rotated about its axis by means of a wheel (J), which is threaded onto the end of a shaft (I). The four screws attached to the tray (F) and a rack and pinion assembly (K) allow for fine positioning of the shell casing in an aperture (H) of the tray. A hinged scoop (L) collects any spherical beads that fall through the aperture during operation.

A counter weight (M) keeps the frame and tray steady during use, while a pivoted handle (N) enables the frame and tray to be rotated for recovery of spherical beads and cleaning. Electrical contact is made via solder terminals (O) to the frame and shaft sleeve, a sprung phosphor bronze contact on the shaft sleeve ensuring electrical contact with the shaft. As the tray is in good electrical and mechanical contact with the frame, there is no requirement for to a soldered contact onto the tray itself.

Clearly, different calibre shell casings require different sized apertures (H) and shafts (I). This is achieved by lifting the tray off the frame, it being held in position by two lugs (P). Similarly, the tapered shaft can be replaced by removing the threaded handle (J) and sliding it from the sleeve. With fingerprints deposited on brass shell casings under laboratory conditions, superior imaging of corrosion has been obtained with this instrument, an example of the corrosion pattern obtained being shown as an inset in FIG. 10.

While the invention has been described in detail and with reference to specific embodiments thereof, it will be apparent to one skilled in the art that various changes and modifications can be made therein without departing from the spirit and scope thereof.

The invention claimed is:

1. A method of detecting a latent fingerprint on a previously heated substrate, the method comprising applying an electrical potential to the substrate, contacting the substrate with detection means attracted to an area of the latent fingerprint and not to areas surrounding the area of the latent fingerprint for detecting said latent fingerprint, and rotating the substrate when contacting the substrate with the detecting means.

2. A method according to claim 1, wherein the area of the latent fingerprint has different electrical properties than the areas surrounding the latent fingerprint.

3. A method according to claim 1, wherein the substrate is brought into contact with support means.

4. A method according to claim 1, wherein contacting the substrate with the detection means is carried out by bringing into contact with the substrate a conductive surface of a delivery means for said detection means.

5. A method according to claim 4, wherein the substrate, a support means and the delivery means are all in electrical contact.

6. A method according to claim 4, comprising adjusting the delivery means to alter the angle between the delivery means and the substrate.

7. A method according to claim 1, wherein the applied potential is approximately 2.5 kV.

8. A method according to claim 1, wherein the detection means has includes conductive powder.

9. A method according to claim 1, wherein the substrate has a tightly curved surface.

10. A method according to claim 1, wherein the substrate is heated subsequent to applying the detection means.

11. Apparatus to detect a latent fingerprint on a substrate, the apparatus comprising delivery means for delivering detection means onto said substrate, support means for supporting the substrate, means for applying an electrical potential to said delivery means and said support means, and means for rotating the substrate as said detection means is delivered onto said substrate.

12. Apparatus according to claim 11, comprising means to retain a substrate within, on or abutting the apparatus.

13. Apparatus according to claim 11, wherein the delivery means is adjustable.

14. Apparatus according to claim 11, wherein the detection means comprises ceramic beads coated with a conductive powder.

15. Apparatus according to claim 11, wherein the electrical potential approximately 2.5 kV.

* * * * *